(12) United States Patent
Jones et al.

(10) Patent No.: US 8,301,268 B1
(45) Date of Patent: *Oct. 30, 2012

(54) IMPLANTABLE ANCHOR WITH ROTATING CAM

(75) Inventors: Robert E. Jones, McKinney, TX (US); Tommy Cushing, Prosper, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 50 days.

This patent is subject to a terminal disclaimer.

(21) Appl. No.: 12/979,709

(22) Filed: Dec. 28, 2010

Related U.S. Application Data

(60) Provisional application No. 61/290,366, filed on Dec. 28, 2009.

(51) Int. Cl.
*A61N 1/00* (2006.01)
(52) U.S. Cl. .................................................. 607/126
(58) Field of Classification Search .................. 607/126, 607/115
See application file for complete search history.

(56) References Cited

U.S. PATENT DOCUMENTS

| | | | | |
|---|---|---|---|---|
| 5,843,146 | A | * | 12/1998 | Cross, Jr. ........................ 607/115 |
| 6,473,654 | B1 | * | 10/2002 | Chinn .............................. 607/126 |

* cited by examiner

*Primary Examiner* — George Manuel
*Assistant Examiner* — Robert N Wieland
(74) *Attorney, Agent, or Firm* — Craig A. Hoersten; Christopher S. L. Crawford

(57) ABSTRACT

There is disclosed various embodiments of an implantable anchor for anchoring a medical lead within a patient. The implantable anchor includes a body having at least one lumen for receiving a medical lead, a cam integrated with the body and rotatable to extend into the lumen for engaging, compressing and twisting the medical lead to inhibit the movement of the lead with respect to the anchor. The body of the anchor may include at least one slot, sized and positioned to receive a portion of the lead to further facilitate the inhibition of the movement of the lead. The cam may include a handle for facilitating the rotation and locking of the cam.

20 Claims, 10 Drawing Sheets

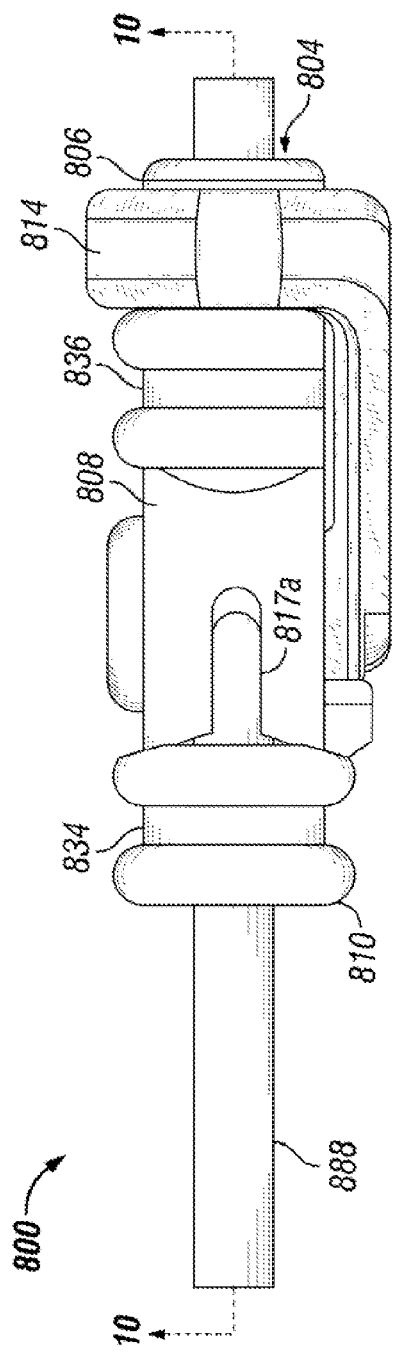
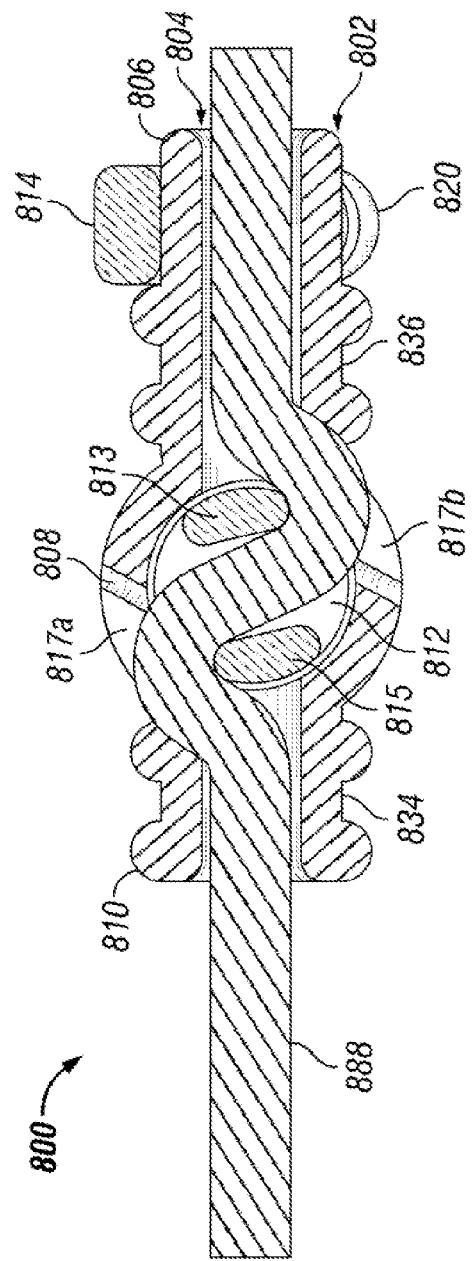
FIG. 9
FIG. 10

IMPLANTABLE ANCHOR WITH ROTATING CAM

CROSS-REFERENCE TO RELATED APPLICATIONS

This application claims the benefit of U.S. Provisional Application No. 61/290,366, filed Dec. 28, 2009, which is incorporated herein by reference.

TECHNICAL FIELD

The present application is generally related to an implantable anchor for anchoring an electrical stimulation lead, a drug infusion catheter or other catheter of an implantable medical device system.

BACKGROUND

A number of implantable medical devices have been commercially distributed that allow various medical agents to be controllably infused after implantation of the respective device within a patient. For example, implantable medical devices are used for the infusion of insulin, opiates, antispasmodic drugs, intrahepatic chemotherapy agents, and other therapeutic agents in a number of countries subject to the regulatory requirements of those countries.

There are a number of benefits to the use of implantable infusion devices. For example, when the therapeutic agent is delivered directly to the therapy site (for opiates and baclofen), the amount of the therapeutic agent that is needed is much lower. Side-effects are generally minimized. Also, the therapeutic effect can be significantly greater as compared to intravenous introduction of therapeutic agents (again, for opiates and baclofen). Furthermore, implantable infusion devices eliminate patient overdosing or underdosing due to patient error or limited patient capacity.

Implantable infusion devices typically include a central housing that includes a reservoir to hold the infusate, a septum to allow infusate to be introduced into the reservoir, an energy source to drive the infusate from the reservoir and through an outlet port, and various flow control elements. The central housing portion of the device is typically implanted in a suitable subcutaneous region with the septum positioned immediately below the skin of the patient to facilitate access to the reservoir for refilling purposes.

To deliver the infusate from the reservoir, a catheter is usually attached to the outlet port of the central housing to receive the infusate outflow. The distal end of the catheter is implanted within the patient adjacent to the appropriate therapy site (e.g., at a suitable intrathecal location to allow introduction of an infusate directly into the spinal fluid of the patient). Typically, some mechanism is employed to anchor the catheter so that infusate will continue to be delivered to the appropriate site such as sutures and/or anchoring structures.

Similar anchoring is also used in spinal cord stimulation (SCS) systems. In SCS systems, a pulse generator is typically implanted within a subcutaneous pocket within the patient. An electrical lead is also implanted within the patient. The proximal end of the electrical lead is electrically coupled (either directly or via one or more extensions) to the pulse generator to receive electrical pulses from the pulse generator. The distal end of the electrical lead is positioned with electrodes of the lead disposed within the epidural space of the patient to deliver the electrical pulses to the spinal neural tissue of the patient. The efficacy of the electrical stimulation in treating chronic pain of the patient depends upon applying the electrical pulses to the appropriate neural tissue. Accordingly, it is desired to retain the stimulation lead at a relatively fixed position over time. For that reason, the electrical lead is anchored so that migration of the electrical lead does not occur.

SUMMARY

Disclosed herein are various embodiments of an implantable anchor for anchoring a medical lead. In one embodiment, the implantable anchor may include a body having a lumen for receiving a medical lead, a rotatable cam is integrated in the body of the anchor and extends into the lumen to interface with the medical lead. When the cam is rotated, the cam rotationally displaces a portion of the medical thereby inhibiting the movement of the lead with respect to the anchor. The cam may include a handle for facilitating the rotation of the cam.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

BRIEF DESCRIPTION OF THE DRAWINGS

FIG. 9 is a top view of the embodiment illustrated in FIG. 8.

FIG. 10 is a cross-sectional view taken along line 10-10 as illustrated in FIG. 9.

DETAILED DESCRIPTION

Figure 1:
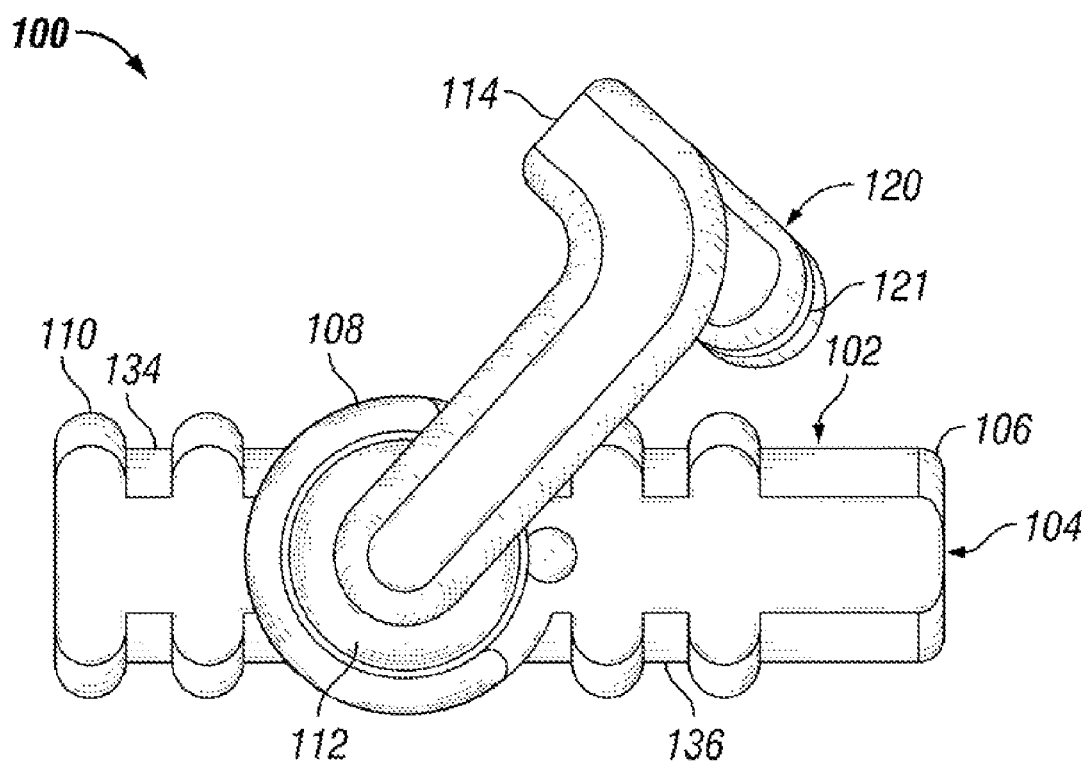
FIG. 1 is a side view illustrating one embodiment of an implantable anchor in a first or open configuration.

For the purposes of promoting an understanding of the principles of the present invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the inventions as described herein are contemplated as would normally occur to one skilled in the art to which the invention relates.

Figure 2:
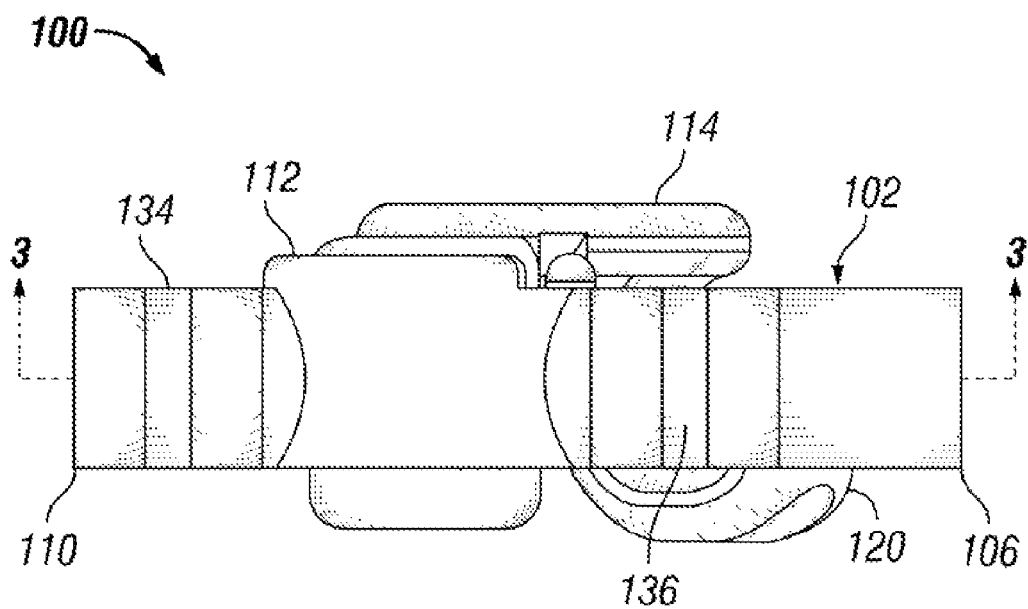
FIG. 2 is a bottom view of the embodiment illustrated in FIG. 1.
Figure 3:
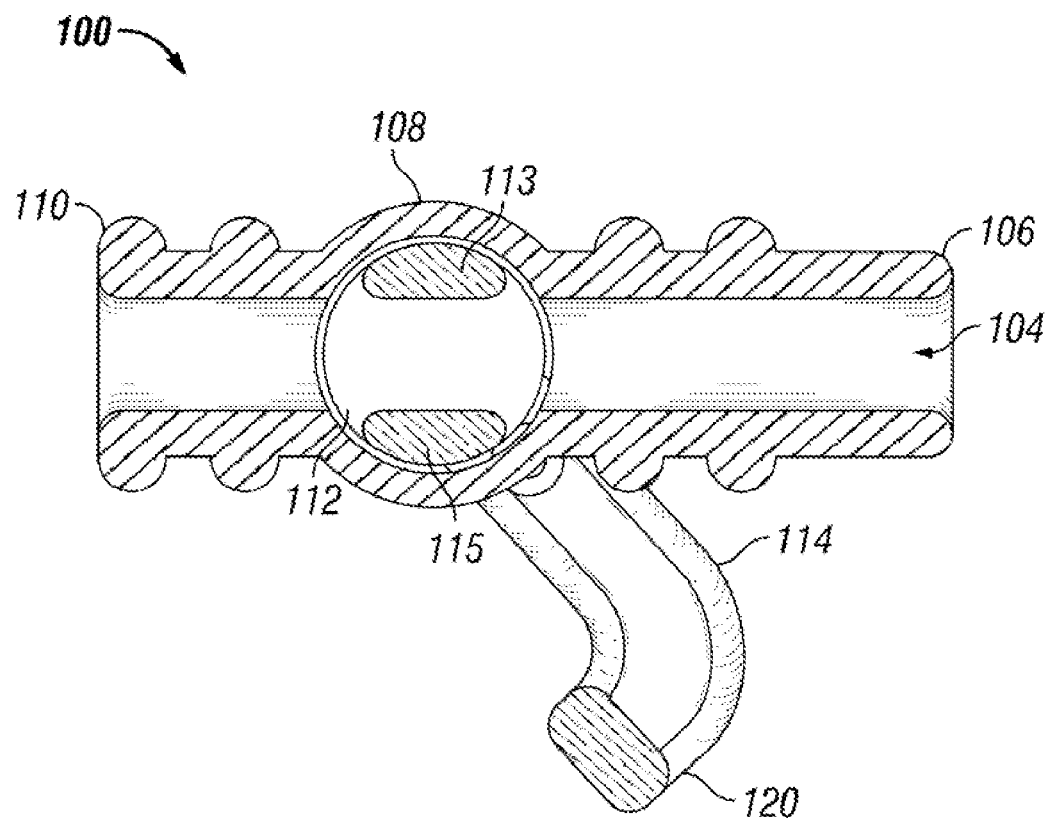
FIG. 3 is a cross-sectional view taken along line 3-3 as illustrated in FIG. 2.
Figure 4:
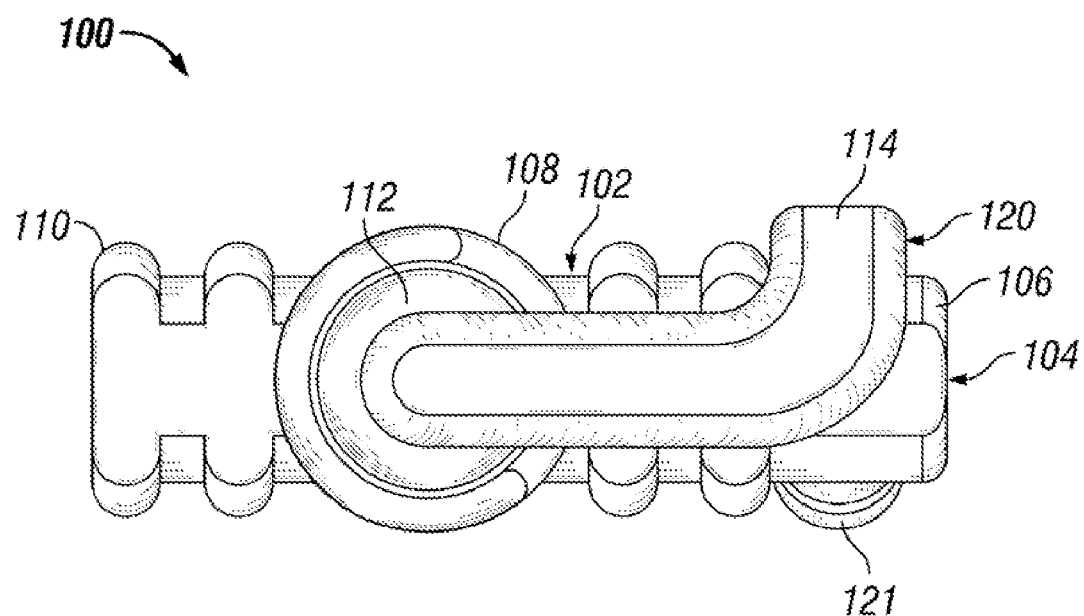
FIG. 4 is a side view illustrating one embodiment of an implantable anchor in a second or closed configuration.
Figure 5:
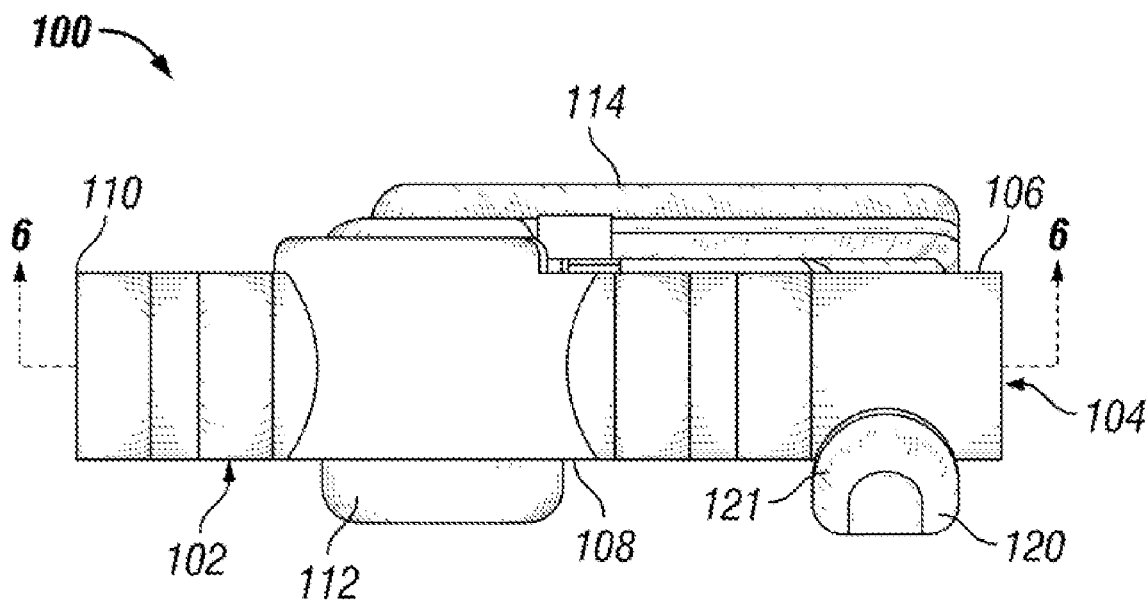
FIG. 5 is a bottom view of the embodiment illustrated in FIG. 4.
Figure 6:
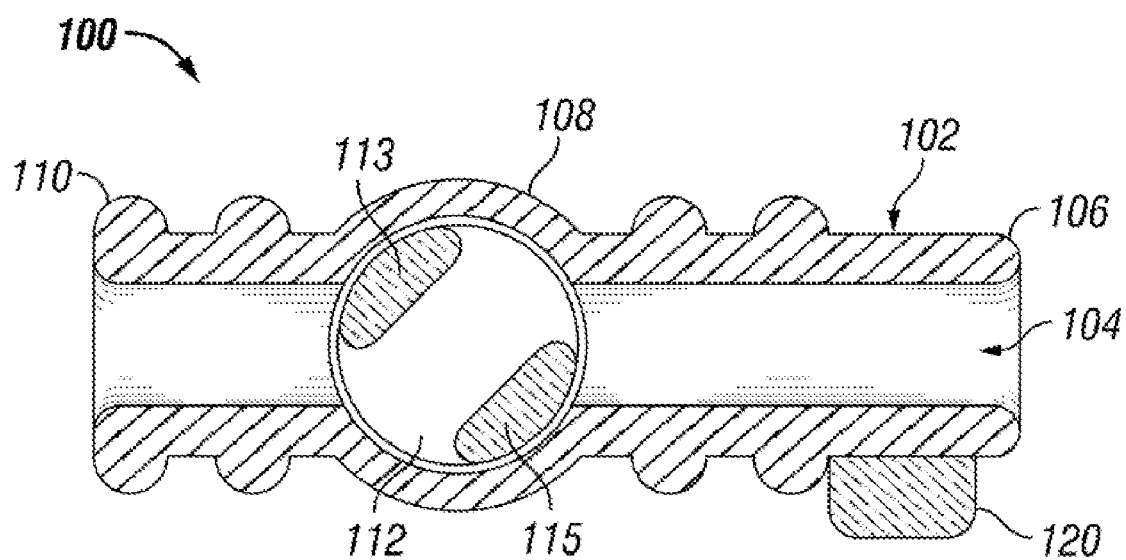
FIG. 6 is a cross-sectional view taken along line 6-6 of the embodiment illustrated in FIG. 5.
Figure 7:
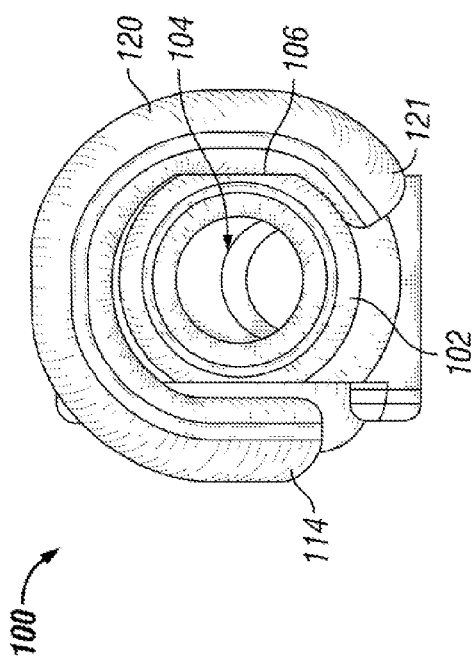
FIG. 7 is an end view of the embodiment illustrated in FIGS. 4, 5, and 6.
Figure 8:
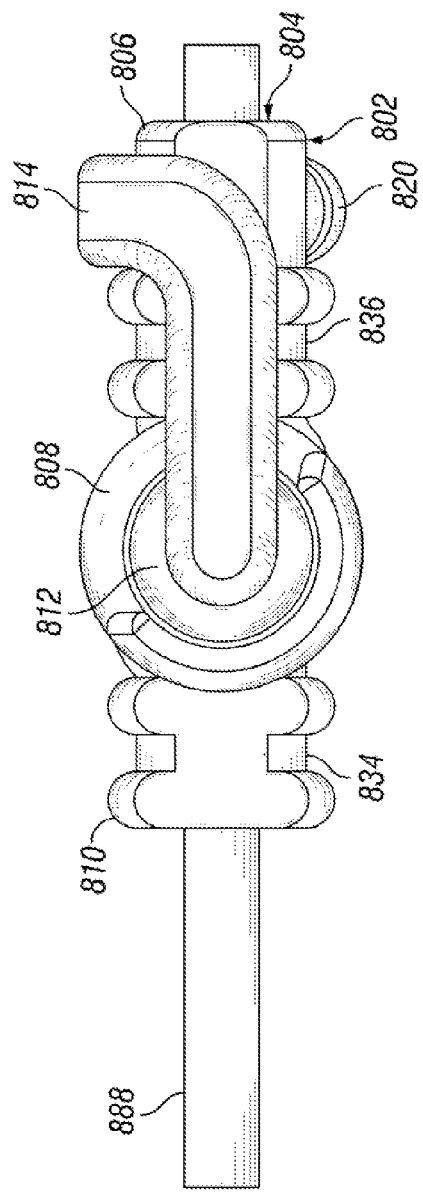
FIG. 8 is a side view illustrating a second embodiment of an implantable anchor.
Figure 11:
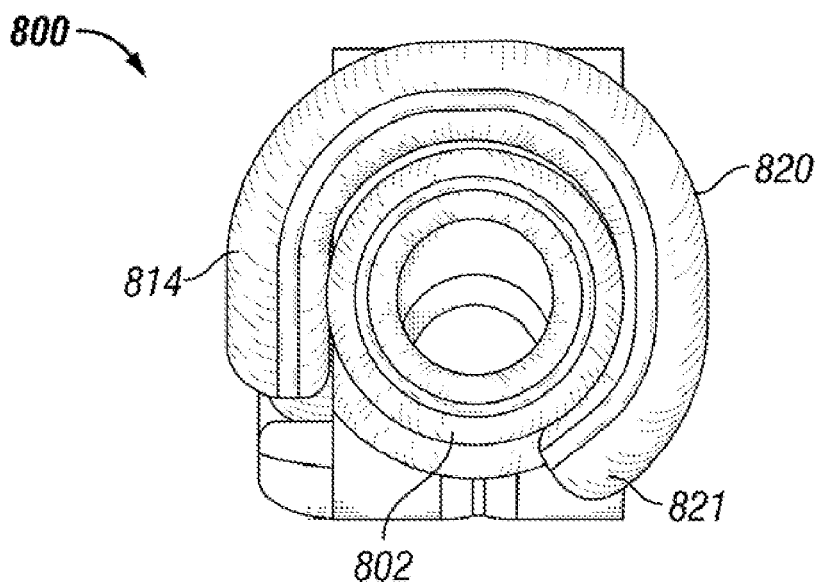
FIG. 11 is an end view of the embodiment illustrated in FIGS. 8, 9 and 10.

FIGS. 1 through 7 depict an implantable anchor 100, with FIGS. 1, 2 and 3 illustrating the anchor 100 in a first or open configuration, and FIGS. 4, 5, 6 and 7 illustrating the anchor 100 in a second or closed configuration. The anchor 100 may be used for anchoring a drug infusion catheter, an electrical lead, or other catheter (not shown) according to one representative embodiment. For the purpose of this disclosure, the term "lead" is used in a broad manner and should be interpreted to encompass both infusion catheters and stimulation leads.

Anchor 100 includes a longitudinal body 102 with a lumen 104 defined therein. Lumen 104 runs from end 106, through middle portion 108 and to end 110 of body 102. As will be explained in greater detail below, the diameter of the longitudinal lumen may be sized accordingly such that a lead of a spinal cord stimulator (SCS) (see FIG. 19) or of an implantable infusion system (see FIG. 20) may slide through body 102.

A rotatable cam 112 is pivotally integrated with middle portion 108 of anchor 100 and extends substantially through body 102. Flanges 113 and 115 (see FIG. 3) of cam 112 are of such a length so as to extend into lumen 104. A handle 114 extends from cam 112 and is used to facilitate the axial rotation of cam 112 in anchor 100. It is contemplated that cam 112 could be configured so as to accept a separate detachable tool to facilitate the axial rotation of cam 112 in anchor 100.

Referring to FIGS. 1-3, when cam 112 is placed in the first or open position, flanges 113 and 115 are positioned so as to permit the insertion of a lead through lumen 104.

As illustrated in FIGS. 4-7, when cam 112 is rotated to the second or closed position, flanges 113 and 115 of cam 112 are rotated into lumen 104 creating a tortuous path, such that when a lead has been previously inserted through lumen 104, flanges 113 and 115 of cam 112 engage the lead extending through lumen 104 thereby substantially inhibiting the movement of the lead with respect to anchor 100.

In operation, anchor 100 is placed in the first position and then placed on an end of a lead and slid over the lead until the anchor 100 is positioned in the desired location along the lead. Cam 112 is then rotated to the second or closed position, such that flanges 113 and 115 of cam 112 engage and displace the lead. Such engagement locks the anchor in place and substantially inhibits movement of the anchor relative to the lead.

Handle 114 includes a generally "C" shaped or hook portion 120 positioned at the end of handle 114, distal to cam 112. Hook portion 120 is shaped with a spring biased tip 121 to engage at least a portion of the perimeter of body 102 at end 106 when anchor 100 is in the second position, thereby locking cam 112 in the closed position securing the lead therein It is contemplated that various other types of locking mechanisms could be implemented in conjunctions with the present invention, so as to lock cam 112 of anchor 100 in the closed position. Such locking mechanisms include without limitation, a ratcheting mechanism or a cam friction lock to further lock cam 112 in the second or closed position, and further inhibit the movement of the anchor relative to the lead.

In certain embodiments, the anchor 100 may be fabricated using any suitable polymer processing technique. The polymer or polymers selected for the anchor 100 are preferably adapted for long term implantation. Biocompatibility and biostability are characteristics for the polymer selection for anchor 100. Also, the polymer preferably possesses a medium to high durometer to maintain the structural characteristics of anchor 100. An example of a suitable polymer for anchor 100 is polyetheretherketone (PEEK), although any biostable, biocompatible polymer having a suitable durometer and a suitable coefficient of friction can be employed.

In one embodiment, a combination of a relatively hard material and a relatively soft (or flexible) material may be utilized. In this embodiment, the middle portion 108 of body 102 may be made from a relatively hard material, such as, but not limited to, select metals or PEEK. One or both of the end portions 106 and 110 may be fabricated from a more compliant material with a lower durometer value such as, but not limited to, silicone. Thus, one or both of the end portions 106 and 110 would be relatively flexible when compared to the middle portion 108 and would act as strain relief ports with respect to the middle portion 108.

In other embodiments, the longitudinal body 102 may be formed from a single piece of material. In such embodiments, the end portions may still function as strain relief ports. However, in these embodiments, the relative flexibility of the end portions may be due to geometric properties (such as thickness of the walls, etc.) and not from the different material properties of the component portions. Thus, the term flexibility as used herein may mean deformable (whether by choice of materials or geometry).

As illustrated, body 102 includes channels 134 and 136 which circumscribe a substantial portion of body 102. Channels 134 and 136 are used to receive sutures therein when suturing anchor 100 to tissue or other parts of the patient.

The diameter of lumen 104 is sufficiently large to permit the introduction of a lead with little difficulty. Thus, when the cam 112 is in the open position (FIG. 3), the anchor 100 may be freely moved along the lead (not shown). However, when the cam 112 is rotated to the second or closed position (FIG. 4), the portion of lumen 104 that passes through cam 112 is rotationally displaced. Thereby, upon rotation of cam 112 from an open to a closed position, the lead is engaged and displaced to cause anchor 100 to hold the lead in place.

Figure 12:
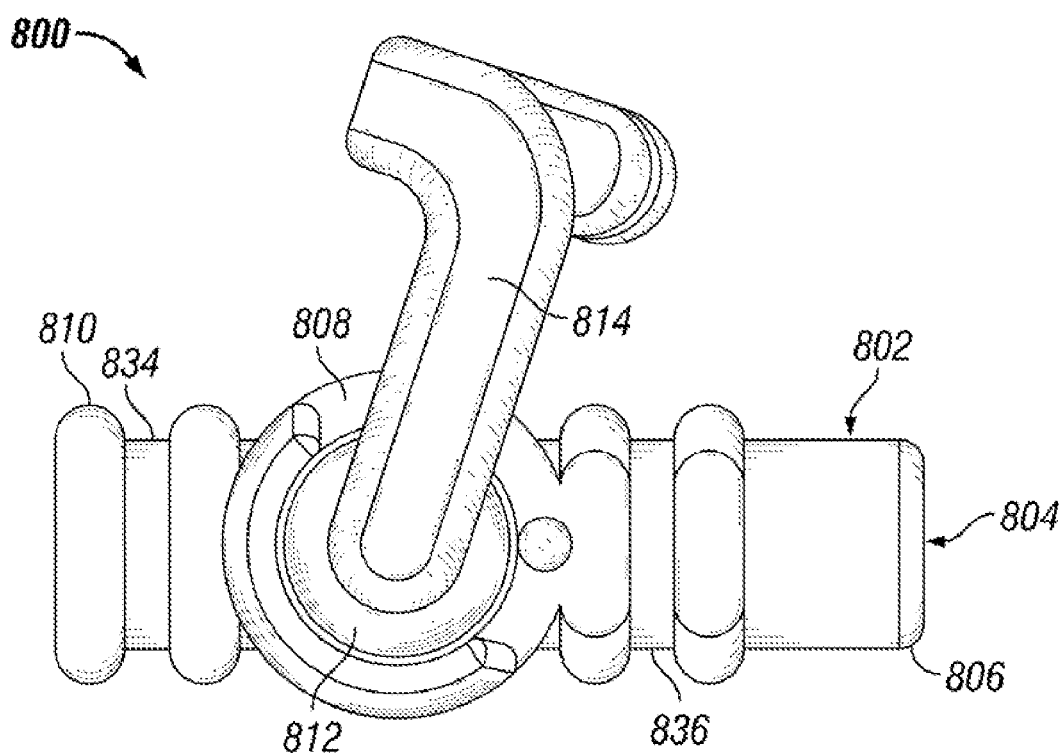
FIG. 12 is a side view illustrating the embodiment illustrated in FIGS. 8, 9 and 10 in an open configuration.
Figure 13:
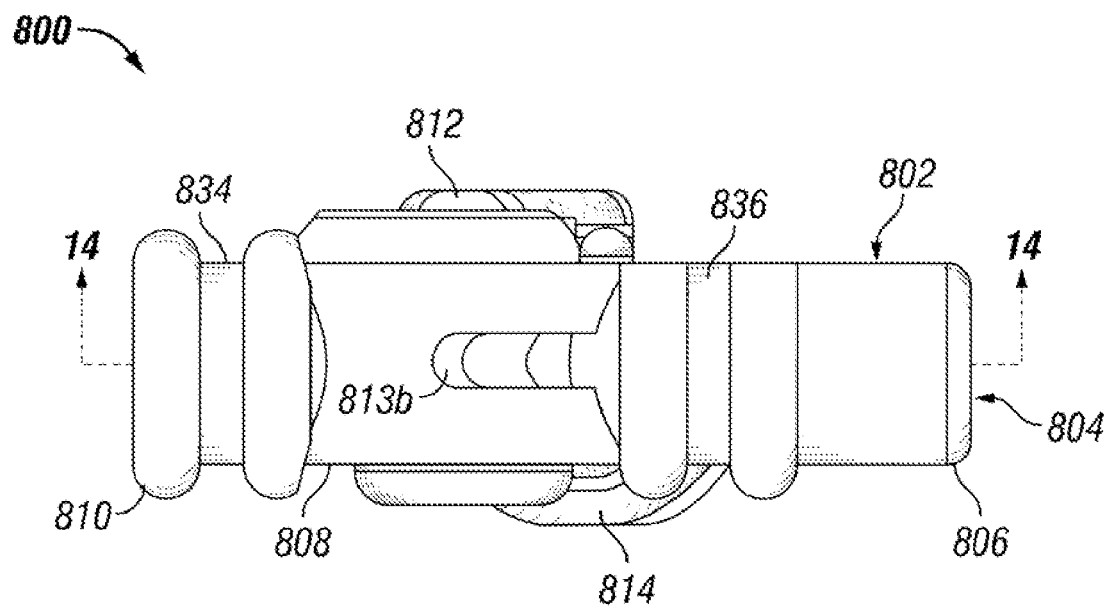
FIG. 13 is a bottom view of the embodiment illustrated in FIG. 12.
Figure 14:
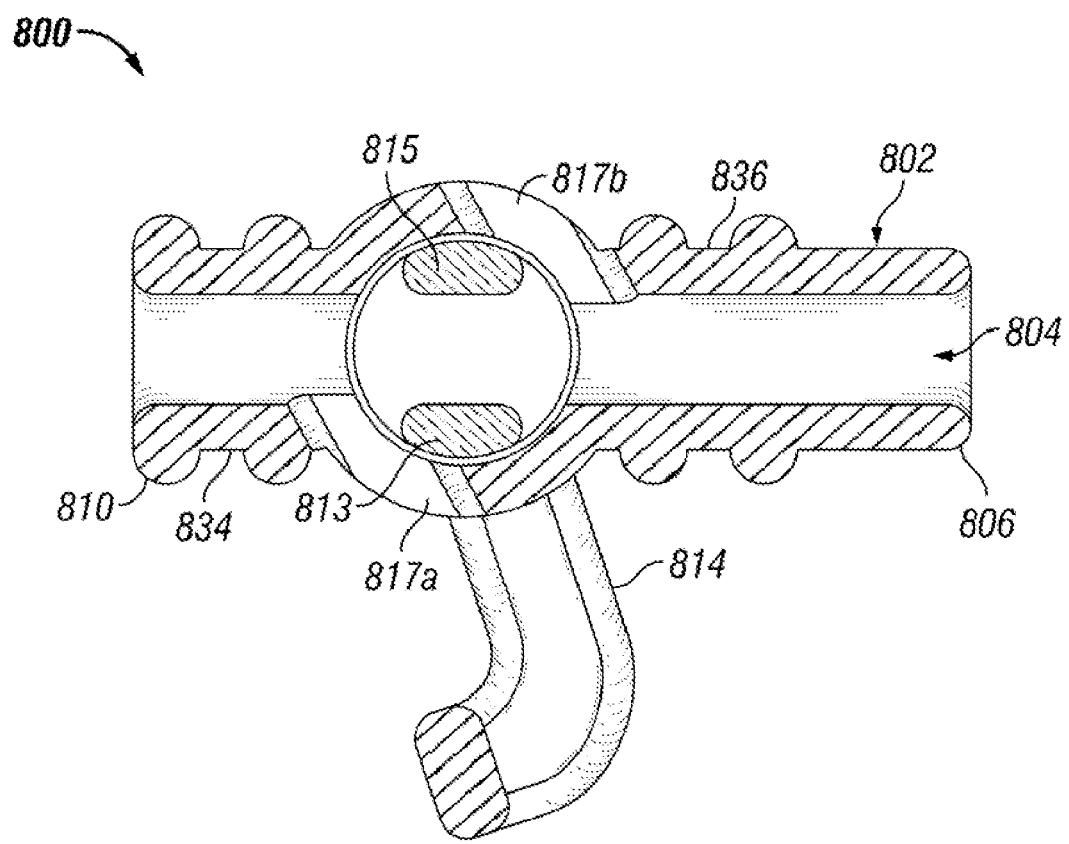
FIG. 14 is a longitudinal cross-sectional view taken along line 14-14 of the embodiment illustrated in FIG. 13.
Figure 15:
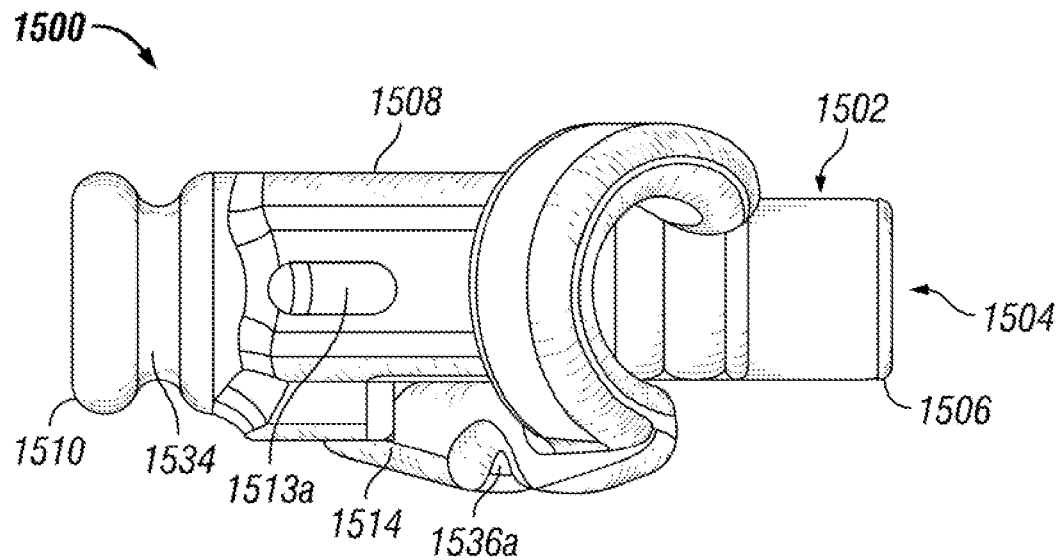
FIG. 15 is a top view illustrating of a third embodiment of an implantable anchor.
Figure 16:
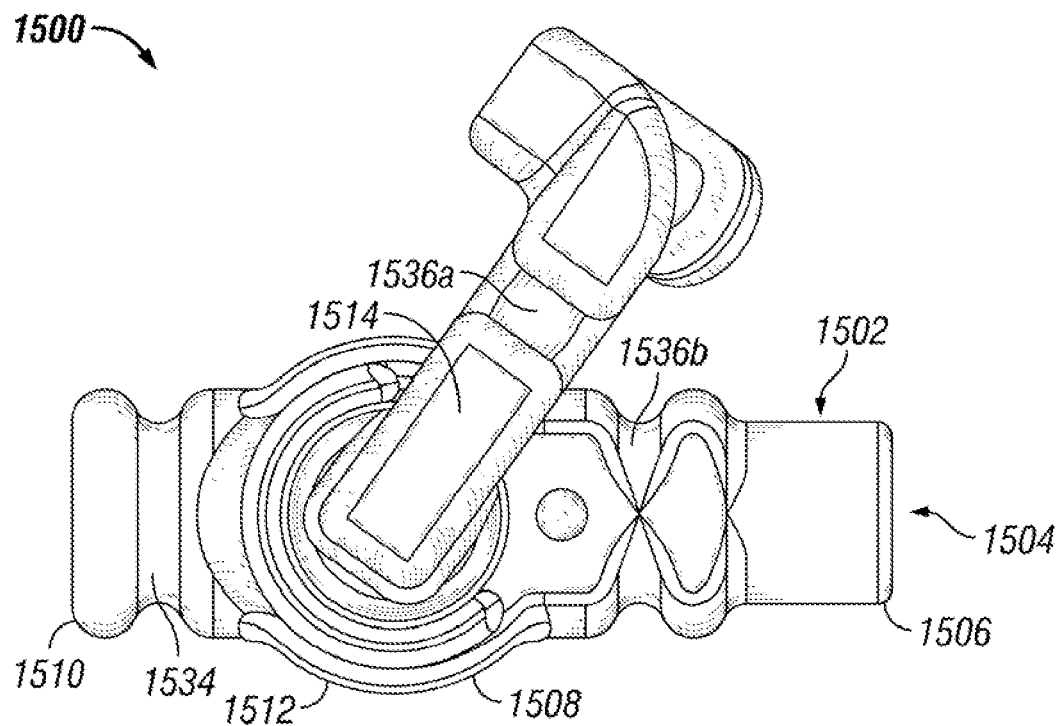
FIG. 16 is a side view of the embodiment as similarly illustrated in FIG. 15.
Figure 17:
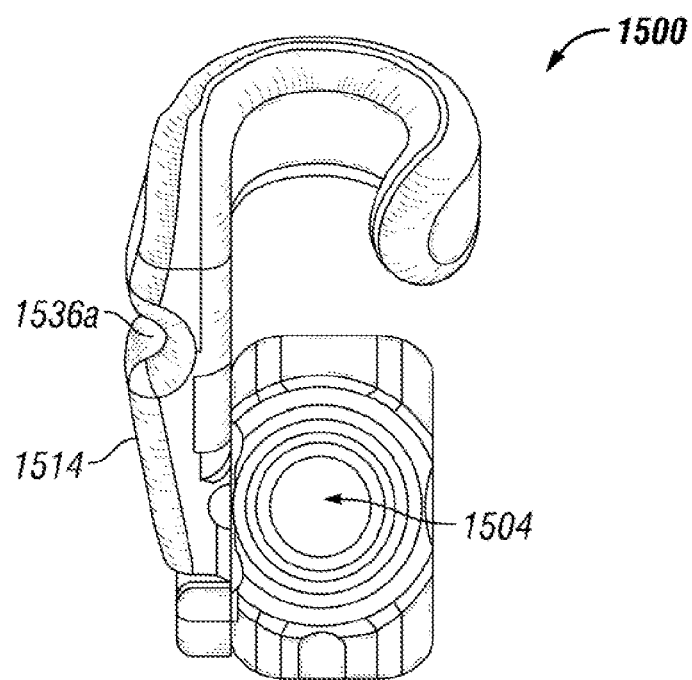
FIG. 17 is an end view of the embodiment illustrated in FIG. 15.
Figure 18:
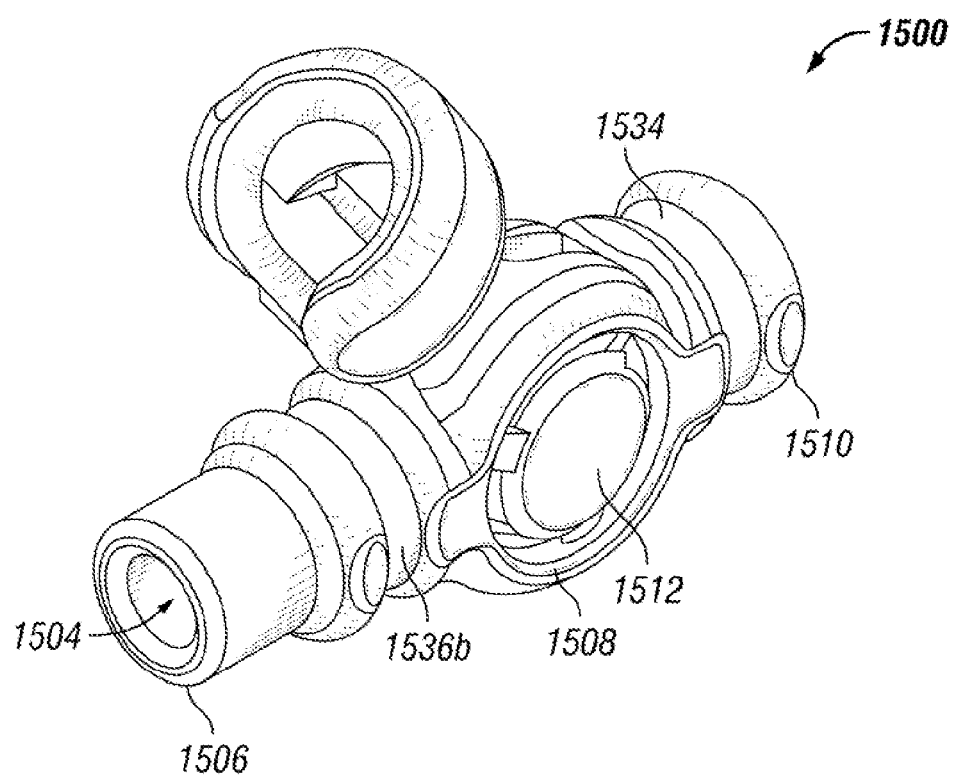
FIG. 18 is an isometric view of the embodiment illustrated in FIG. 15.

Referring now to FIGS. 8 through 14, there is depicted an implantable anchor 800 according to an alternative embodiment of the present invention. FIGS. 8, 9, 10 and 11 illustrate the anchor 800 in a second or closed configuration, while FIGS. 12, 13 and 14 illustrate the anchor 800 in a first or open configuration. The anchor 800 may be used for anchoring a drug infusion catheter, an electrical lead, or other catheter (not shown) according to one representative embodiment. It is contemplated the term "lead" is used in a broad manner and should be interpreted to encompass both infusion catheters and stimulation leads.

Anchor 800 includes a longitudinal body 802 with a lumen 804 defined therein. Lumen 804 runs from end 806, through middle portion 808 and to end 810 of body 802. As will be explained in greater detail below, the diameter of the longitudinal lumen may be sized accordingly such that a lead of a spinal cord stimulator (SCS) (see FIG. 19) or of an implantable infusion system (see FIG. 20) may slide through body 802.

A rotatable cam 812 is pivotally integrated with middle portion 808 of anchor 800 and extends substantially through body 802. Flanges 813 and 815 (see FIGS. 10 and 14) of cam 812 are of such a length so as to extend into lumen 804. A handle 814 extends from cam 812 and is used to facilitate the axial rotation of cam 812 in anchor 800. It is contemplated that cam 812 could be configured so as to accept a separate detachable tool to facilitate the axial rotation of cam 812 in anchor 800.

Middle portion 808 includes slot 817a and slot 817b (see FIG. 10), which slots 817a and 817b are dimensioned so as to be of a smaller size that the diameter of lead 888, as will be discussed in further detail below.

Referring to FIGS. 12, 13 and 14, when cam 812 is placed in the first or open position, flanges 813 and 815 are positioned so as to permit the insertion of a lead through lumen 804.

As illustrated in FIGS. 8-11, when cam 812 is rotated to the second or closed position, flanges 813 and 815 of cam 812 are rotated into lumen 804 creating a tortuous path with flanges 813 and 815 of cam 812 engaging lead 888, thereby substantially inhibiting the movement of the lead 888 with respect to anchor 800 (see FIG. 10). When cam 812 engages and displaces the portion of lead 888 that passes through cam 812, a portion of lead 888 extends into both slots 817a and 817b, thereby further inhibiting the longitudinal and lateral movement of the lead 888 with respect to anchor 800.

In operation, anchor 800 is placed in the first position and then placed on an end of lead 888 and slid over the lead until the anchor 800 is positioned in the desired location along the lead. Cam 812 is then rotated to the second or closed position, such that flanges 813 and 815 of cam 812 engage and displace lead 888, and further force portions of lead 888 into slots 817a and 817b. Such engagement locks the anchor 800 in place and substantially inhibits movement of the anchor 800 relative to the lead 888.

Handle 814 includes a generally "C" shaped or hook portion 820 positioned at the end of handle 814, distal to cam 812. Hook portion 820 is shaped with a spring biased tip 821 to engage at least a portion of the perimeter of body 802 at end 806 when anchor 800 is in the second position, thereby locking cam 812 in the closed position securing the lead 888 therein.

It is contemplated that various other types of locking mechanism could be implemented in conjunction with the present invention, so as to lock cam 812 of anchor 800 in the closed position. Such locking mechanisms include, without limitation, a ratcheting mechanism or a cam friction lock may be utilized to further lock cam 812 in the second or closed position, and further inhibit the rotation of cam 812 from the second position back to the first position.

In certain embodiments, the anchor 800 may be fabricated using any suitable polymer processing technique. The polymer or polymers selected for the anchor 800 are preferably adapted for long term implantation. Biocompatibility and biostability are characteristics for the polymer selection for anchor 800. Also, the polymer preferably possesses a medium to high durometer to maintain the structural characteristics of anchor 800. An example of a suitable polymer for anchor 800 is polyetheretherketone (PEEK), although any biostable, biocompatible polymer having a suitable durometer and a suitable coefficient of friction can be employed.

In one embodiment, a combination of a relatively hard material and a relatively soft (or flexible) material may be utilized. In this embodiment, the middle portion 808 of body 802 may be made from a relatively hard material, such as, but not limited to, select metals or PEEK. One or both of the end portions 806 and 810 may be fabricated from a more compliant material with a lower durometer value such as, but not limited to, silicone. Thus, one or both of the second end portions 806 and 810 would be relatively flexible when compared to the middle portion 808 and may act as strain relief ports with respect to the middle portion 808.

In other embodiments, the longitudinal body 802 may be formed from a single piece of material. In such embodiments, the end portions may still function as strain relief ports. However, in these embodiments, the relative flexibility of the end portions may be due to geometric properties (such as thickness of the walls, etc.) and not from the different material properties of the component portions. Thus, the term flexibility as used herein may mean deformable (whether by choice of materials or geometry).

As illustrated, body 802 includes channels 834 and 836 which generally circumscribe body 802. Channels 834 and 836 are used to facilitate the suturing of anchor 800 to tissue of the patient.

The diameter of lumen 804 is sufficiently large to permit the introduction of a lead with little difficulty. Thus, when the cam 812 is in the first or open position, the anchor 800 may be freely moved along the lead 888. However, when the cam 812 is rotated to the second or closed position (FIG. 10), the portion of lumen 804 that passes through cam 812 is rotationally displaced. Thereby, upon rotation of cam 812 from an open to a closed position, the lead 888 is engaged and displaced, and a portion of the lead 888 is forced into slots 817a and 817b, to cause anchor 800 to hold the lead 888 in place.

Referring now to FIGS. 15 through 18, there is depicted an implantable anchor 1500 according to an alternative embodiment. The anchor 1500 includes a longitudinal body 1502 with a lumen 1504 defined therein. In the illustrative embodiment, lumen 1504 runs longitudinally between ends 1506 and 1510, through middle portion 1508.

As similarly shown and described herein with reference to the embodiment illustrated in FIGS. 1-7, anchor 1500 includes a rotatable cam 1512 that extends laterally through anchor 1500. A handle or arm 1514 is integrated with cam 1512, with the handle 1514 for facilitating the axial rotation of cam 1512 in anchor 1500. Cam 1512 is similar in design and operation to cams 112 and 812 described herein, and is operable between a first or open position and a second or closed position.

In the illustrative embodiment, handle 1514 includes a notch or channel 1536a, and longitudinal body 1502 includes a channel 1536b. Channels 1536a and 1536b are configured such that when handle 1514 is placed in a second or closed position, channel 1536a aligns with channel 1536b. It is contemplated that when channel 1536a and channel 1536b are so aligned, the resulting alignment may be used for at least one of tying a suture to anchor 1500 so as to further retain handle 1514 in the second or closed position and/or suturing anchor 1500 to tissue of the patient.

Figure 19:
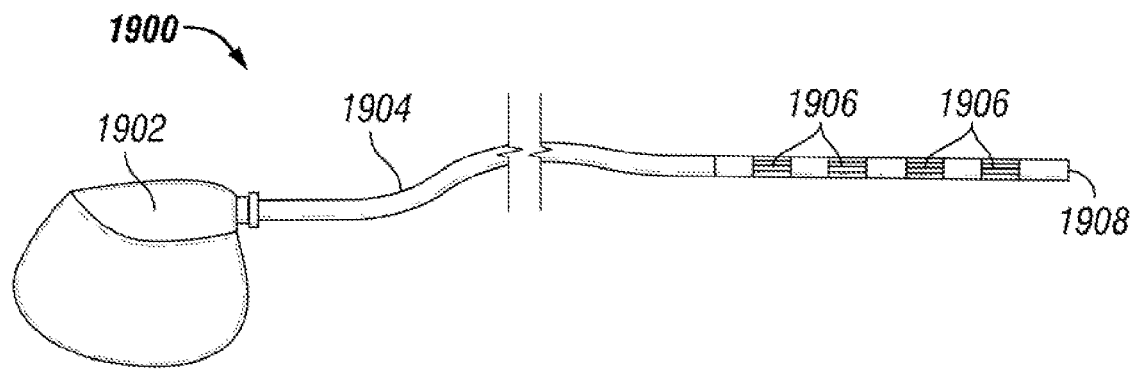
FIG. 19 depicts a conventional neurostimulation system that may utilize an anchor according to at least one representative embodiment.

Anchors according to representative embodiments may be utilized in conjunction with any suitable implantable medical device that comprises an implantable lead. For example, anchors 100, 800, and 1500 can be utilized to anchor a stimulation lead of a neurostimulation system as shown in FIG. 19. A neurostimulation system 1900 includes a pulse generator 1902 and one or more stimulation leads 1904.

The pulse generator 1902 is typically implemented using a metallic housing that encloses circuitry for generating the electrical pulses for application to neural tissue of the patient. The pulse generator 1902 is usually implanted within a subcutaneous pocket created under the skin by a physician. The lead 1904 is used to conduct the electrical pulses from the implant site of the pulse generator for application to the targeted nerve tissue via electrodes 1906. The lead 1904 typically includes a lead body of an insulative polymer material with embedded wire conductors extending through the lead body. The electrodes 1906 of the lead body are coupled to the conductors to deliver the electrical pulses to the nerve tissue. For example, the distal end 1908 of lead 1904 may be positioned within the epidural space of the patient to deliver electrical stimulation to spinal nerves to treat chronic pain of the patient. The anchors disclosed herein may, among other things, be utilized to ensure that the distal end 1908 of the lead 1904 remains adjacent to the appropriate nerves associated with the chronic pain of the patient. In some embodiments, an "extension" lead (not shown) may be utilized as an intermediate connector if deemed appropriate by the physician.

In certain embodiments for SCS applications, the lead 1904 is a "body compliant" lead that possesses mechanical characteristics that allow the lead 1904 to stretch in response to forces experienced with the patient's body. For example, the lead 1904 may be adapted to stretch up to 25% in response to low stretching forces such as 2-2 pounds of force. The ability to exhibit significant elongation in response to such low forces enables the lead to be relatively robust (e.g., does not experience significant conductor breakage). Fabrication techniques and material characteristics for "body compliant" leads are disclosed in greater detail in U.S. Provisional Patent Application Ser. No. 60/788,518, entitled "Lead Body Manufacturing," filed Mar. 31, 2006, which is incorporated herein by reference for all purposes.

Figure 20:
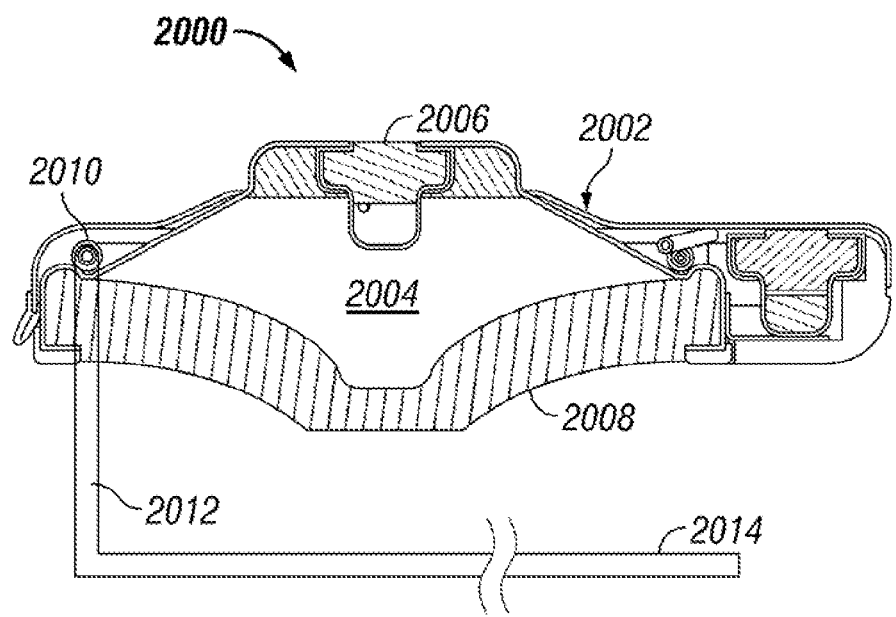
FIG. 20 depicts a conventional drug pump system that may utilize an anchor according to at least one representative embodiment.

Alternatively, the anchors 100, 800, and 1500 can be utilized to anchor an infusion catheter of an implantable drug infusion device 2000 as shown in FIG. 20. The implantable infusion drug pump device 2000 may include a central housing 2002, a reservoir 2004 to hold the infusate, a septum 2006 to allow infusate to be introduced into the reservoir, an energy source 2008 (e.g., a spring diaphragm) to drive the infusate from the reservoir and through an outlet port 2010, and various flow control elements (not shown).

The central housing 2002 of the device is often implanted in a suitable subcutaneous region with the septum 2006 positioned immediately below the skin of the patient to facilitate access to the reservoir 2004 for refilling purposes. A catheter 2012 is attached to the outlet port 2010 of the central housing 2002 to receive the infusate outflow. A distal end 2014 of the catheter is implanted within the patient adjacent to the appropriate therapy site. The anchors 100, 800, and 1500 may be utilized to ensure that the distal end 2014 of the lead 2012 remains adjacent to the appropriate site generating the chronic pain of the patient.

Although some representative embodiments have been discussed in terms of anchoring intrathecal and epidural catheters and leads, anchors can be employed according to alternative embodiments for any suitable location. For example, an anchor according to some embodiments could be used for peripheral nerve stimulation and gastric pacing applications.

Although representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure that processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

Any combination of the features discussed above is within the scope of certain embodiments of the present invention. Thus, a feature disclosed in reference to one embodiment may be combined with another embodiment. Furthermore, combinations of disclosed features and alternative features are within the scope of certain embodiments of the present invention.

The abstract of the disclosure is provided for the sole reason of complying with the rules requiring an abstract, which will allow a searcher to quickly ascertain the subject matter of the technical disclosure of any patent issued from this disclosure. It is submitted with the understanding that it will not be used to interpret or limit the scope or meaning of the claims.

What is claimed is:

1. An implantable anchor for anchoring a medical lead within a user, the anchor comprising:
    a body having at least a first lumen, the lumen extending from a first end of the body to a second end of the body along an axis, the lumen configured to receive the medical lead, the body having a cavity extending into the body generally perpendicular to the axis of the lumen; and
    a cam including a first flange, the cam rotatably mounted within at least portion of the cavity of body intermediate the first end and the second end of the body, the cam rotatable between at least a first position and a second position, such that when the cam is in the first position, the first flange of the cam is substantially free from the lumen, such to facilitate the insertion and movement of the medical lead into the anchor, and further when the cam is in the second position, at least a portion of the flange of the cam extends into the lumen, such that when the medical lead extends through the lumen, the first flange of the cam displaces a section of the medical lead to substantially inhibit the movement of the medical lead with respect to the anchor.

2. The implantable anchor of claim 1, and further including an arm extending from the cam, the arm for facilitating the rotation of the cam between the first and second positions.

3. The implantable anchor of claim 1, further including a locking mechanism for locking the cam in the second position.

4. The implantable anchor of claim 2, wherein the arm includes a portion configured to engage the body to the anchor to releasably lock the cam in the second position.

5. The implantable anchor of claim 4, wherein the cam includes a second flange, the second flange positioned to extend into the lumen, the second flange for displacing the medical lead when the cam is positioned in the second position.

6. The implantable anchor of claim 4, wherein at least a portion of the engagement portion of the arm is configured in generally a "C" shape.

7. The implantable anchor of claim 1, wherein said body includes a slot for receiving a portion of the medical lead when the first flange of the cam twists the medical lead.

8. The implantable anchor of claim 1, wherein the body includes a plurality of slots, each of the plurality of slots for receiving a portion of the medical lead when the first flange of the cam displaces the section of the medical lead.

9. An implantable anchor for anchoring a medical lead within a living organism, the anchor comprising:
an elongated body having at least one lumen, the at least one lumen extending intermediate a first end of the body and a second end of the body along an axis, the at least one lumen configured to receive the medical lead, the body having a cavity extending into the body generally perpendicular to the axis of the lumen; and
a cam including at least one flange, with at least a portion of the cam positioned within the cavity of the body, the cam rotatable between at least a first position and a second position, such that when the cam is in the first position, the at least one flange of the cam is substantially free from the lumen, such to facilitate the insertion and movement of the medical lead into the anchor, and further when the cam is in the second position, at least a portion of the flange of the cam extends into the lumen, such that the at least one flange displaces a section of a medical lead extending through the lumen to substantially inhibit the movement of the medical lead with respect to the anchor.

10. The implantable anchor of claim 9, and further including an arm extending from the cam, the arm for facilitating the rotation of the cam between the first and second positions.

11. The implantable anchor of claim 9, further including a locking mechanism for locking the cam in the second position.

12. The implantable anchor of claim 10, wherein the arm includes a portion configured to engage the body to the anchor to lock the cam in the second position.

13. The implantable anchor of claim 9, wherein the cam includes at least a second flange, the second tab positioned to extend into the lumen, the second flange for displacing the section the medical lead when the cam is positioned in the second position.

14. The implantable anchor of claim 12, wherein at least a portion of the engagement portion of the arm is configured in generally a "C" shape.

15. The implantable anchor of claim 9, wherein said body includes at least one slot for receiving a portion of the medical lead when the first flange of the cam displaces the section of the medical lead.

16. An implantable anchor for anchoring a medical lead within a living organism, the anchor comprising:
an elongated body having at least one lumen, the at least one lumen extending intermediate a first end of the body and a second end of the body along an axis, the at least one lumen configured to receive the medical lead, the body having a cavity extending into the body generally perpendicular to the axis of the lumen;
a cam connected to the body, the cam rotatable between a first position and a second position; and
a plurality of flanges connected to the cam, such that when the cam is in the first position, each of the plurality of flanges are substantially free from the lumen, such to facilitate the insertion and movement of the medical lead into the anchor, and further when the cam is in the second position, each of the plurality of flanges displaces a section of the medical lead extending through the lumen to substantially inhibit the movement of the medical lead with respect to the anchor.

17. The implantable anchor of claim 16, and further including an arm extending from the cam, the arm for facilitating the rotation of the cam between the first and second positions.

18. The implantable anchor of claim 17, further including a locking mechanism for locking the cam in the second position.

19. The implantable anchor of claim 18, wherein the locking mechanism includes a portion extending from the arm configured to engage the body to the anchor.

20. The implantable anchor of claim 19, wherein said body includes at least one slot for receiving a portion of the medical lead when the plurality of flanges displaces the section of the medical lead.

* * * * *